United States Patent
Luker

[19]

[11] Patent Number: 5,888,453
[45] Date of Patent: Mar. 30, 1999

[54] CONTINUOUS FLOW PASTEURIZATION OF SEWAGE SLUDGE

[75] Inventor: Michael A. Luker, Menifee, Calif.

[73] Assignee: Riverside County Eastern Municipal Water District, Perris, Calif.

[21] Appl. No.: 792,692

[22] Filed: Jan. 29, 1997

[51] Int. Cl.[6] .................................................. A61L 2/00
[52] U.S. Cl. ........................ 422/38; 165/901; 165/902; 210/175; 210/179; 210/180; 422/1; 422/307; 422/308
[58] Field of Search ................................. 422/307, 308, 422/1, 38; 210/175, 179, 180; 165/901, 902

[56] References Cited

U.S. PATENT DOCUMENTS

| | | | |
|---|---|---|---|
| 2,190,598 | 2/1940 | Fischer | 210/2 |
| 2,613,180 | 10/1952 | Green et al. | 210/2 |
| 2,847,379 | 8/1958 | Spiegel et al. | 210/6 |
| 2,998,139 | 8/1961 | Novak | 210/97 |
| 3,296,122 | 1/1967 | Karassik et al. | 210/2 |
| 3,337,448 | 8/1967 | Rich | 210/3 |
| 3,535,234 | 10/1970 | Gilwood | 210/7 |
| 3,821,107 | 6/1974 | Peoples | 210/12 |
| 4,092,338 | 5/1978 | Tossey | 210/142 |
| 4,274,838 | 6/1981 | Dale et al. | 48/111 |
| 4,511,370 | 4/1985 | Hunziker et al. | 48/197 |
| 4,582,607 | 4/1986 | Kiese et al. | 210/612 |
| 4,925,571 | 5/1990 | Jacob et al. | 210/742 |
| 4,988,442 | 1/1991 | Highsmith et al. | 210/609 |
| 5,034,131 | 7/1991 | Stenroos et al. | 210/612 |
| 5,417,937 | 5/1995 | Voigt et al. | 422/189 |
| 5,480,540 | 1/1996 | Day et al. | 210/181 |

*Primary Examiner*—Krisanne Thornton
*Attorney, Agent, or Firm*—Baker & Maxham

[57] ABSTRACT

A continuous flow sludge pasteurization system including a heat exchanger, a source of heat for introducing into the heat exchanger, an inlet for introducing a liquid slurry of sludge into the heat exchanger for heating the sludge to a predetermined minimum temperature, a circulating circuit for maintaining the slurry in circulation at the predetermined temperature for a minimum period of about thirty minutes, sufficient to kill all pathogens in the slurry prior to dewatering, and a dewatering unit for removing water from the sludge.

20 Claims, 2 Drawing Sheets

CONTINUOUS FLOW PASTEURIZATION OF SEWAGE SLUDGE

BACKGROUND OF THE INVENTION

The present invention relates to the processing of sewage sludge and pertains particularly to improved method and apparatus for processing municipal sewage sludge for eliminating pathogens.

Densely populated areas of the world, such as cities, produce waste collected and treated as sewage that must be disposed of in a reasonably sanitary manner in order to protect public health. Most cities have sewer systems which collect and carry raw sewage, flushed by water to collection and treatment plants. The raw sewage is normally treated at various levels including anaerobic and/or aerobic digestion and sludge resulting from the treatment is disposed of in various manners including in land fills. A small percentage of it is disposed of on agricultural land. Disposal of the sludge is a problem because it contains all of the disease organisms common to man. Raw sewage collected at sewage treatment plants is normally first subjected to a primary treatment by settling and screening to dispose of sand, grit and some soluble solids. The settled solids are undigested raw sludge and normally pumped to aerobic digester where the raw sludge is converted to an organically stable form. The settled sewage is subjected to secondary treatment, where microorganisms are introduced with an excess of oxygen utilizing aeration. This secondary treatment results in digestion of the settled solids, aerobically and/or anaerobically. The resulting solids and treatment additives are separated or settled out and the sludge is removed for further processing.

The material that settles out is digested to further stabilize organic matter in the sludge solids. This treated sludge is dewatered and the sludge is then typically disposed of by commercial processors who are paid by the treatment plant to dispose of the sludge. The commercial processors further treat the sludge by composting it so that it can then be used for fertilizer or soil amendment. This amounts to an enormous cost to the treatment plant.

In the past, much of the sludge has been used in land fills or has been dumped in the ocean. These means of disposal are no longer permitted because of health and environmental concerns. A considerable effort has been undertaken to provide appropriate means of disposing of sludge without harming the population or the environment. Many techniques have been proposed for treating raw sludge to allow for disposal, such as dewatering and subsequent incineration. However, incineration introduces its own problems, such as air pollution from the burning of the sludge.

Many efforts are underway to recover the sludge and use it as a resource for its nutrient value for land application as fertilizer or soil amendment. Proposals have been made, for example, for its use in desert land reclamation. However, pathogens in the sludge must be removed before its application in or near populated areas where it is likely to be contacted by humans or animals.

Present concerns for public health require that the sludge be further processed if it is to be used as a fertilizer or as a soil conditioner, such as in land rock reclamation projects. This further treatment is required because the typical sludge product of a treatment plant still contains substantial quantities of bacteria, viruses and other organisms. One method that has been proposed for eliminating this problem is that of pasteurization. However, this is a costly process requiring expensive plant and equipment and substantial amounts of energy to carry out. Heating the sludge to effectively pasteurize it requires that it be heated to a temperature of at least about 160° F. and maintained at that temperature for a minimum of 30 minutes. This is typically carried out in a batch process in large holding tanks to insure that no short circuiting occurs. Once the sludge has been pasteurized, it is suitable for land fills and land reclamation and low grade fertilizer. However, such pasteurization in this manner is expensive and not cost effective.

Presently known processes for pasteurization, however, are batch processes and are enormously expensive to construct and operate. Pasteurization, however, can ultimately reduce some cost of disposal by reducing the expense of paying commercial disposal companies for disposal of the sludge. Pasteurization can turn the sludge into a resource making it sufficiently desirable that much of the cost can be recovered. However, the pasteurization costs must be sufficiently low to make the whole operation economical.

It is therefore desirable that an inexpensive and cost-effective pasteurization system and process be available.

SUMMARY AND OBJECTS OF THE INVENTION

It is the primary object of the present invention to provide a method and apparatus for continuous processing and pasteurization of sewage.

In accordance with the primary aspect of the present invention, a continuous process pasteurization system comprises a heat exchanger, a source of heat for introducing into said heat exchanger, means for introducing a liquid slurry of sludge into said heat exchanger for heating said sludge to a predetermined minimum temperature, a circulating circuit for maintaining said slurry in circulation at said predetermined temperature for a minimum period, of about thirty minutes, sufficient to kill all pathogens in said slurry, and dewatering means for removing a substantial amount of water from said sludge.

BRIEF DESCRIPTION OF THE DRAWINGS

The above and other objects and advantages of the present invention will become apparent from the following description when read in conjunction with the accompanying drawings wherein.

DETAILED DESCRIPTION OF PREFERRED EMBODIMENTS

Figure 1:
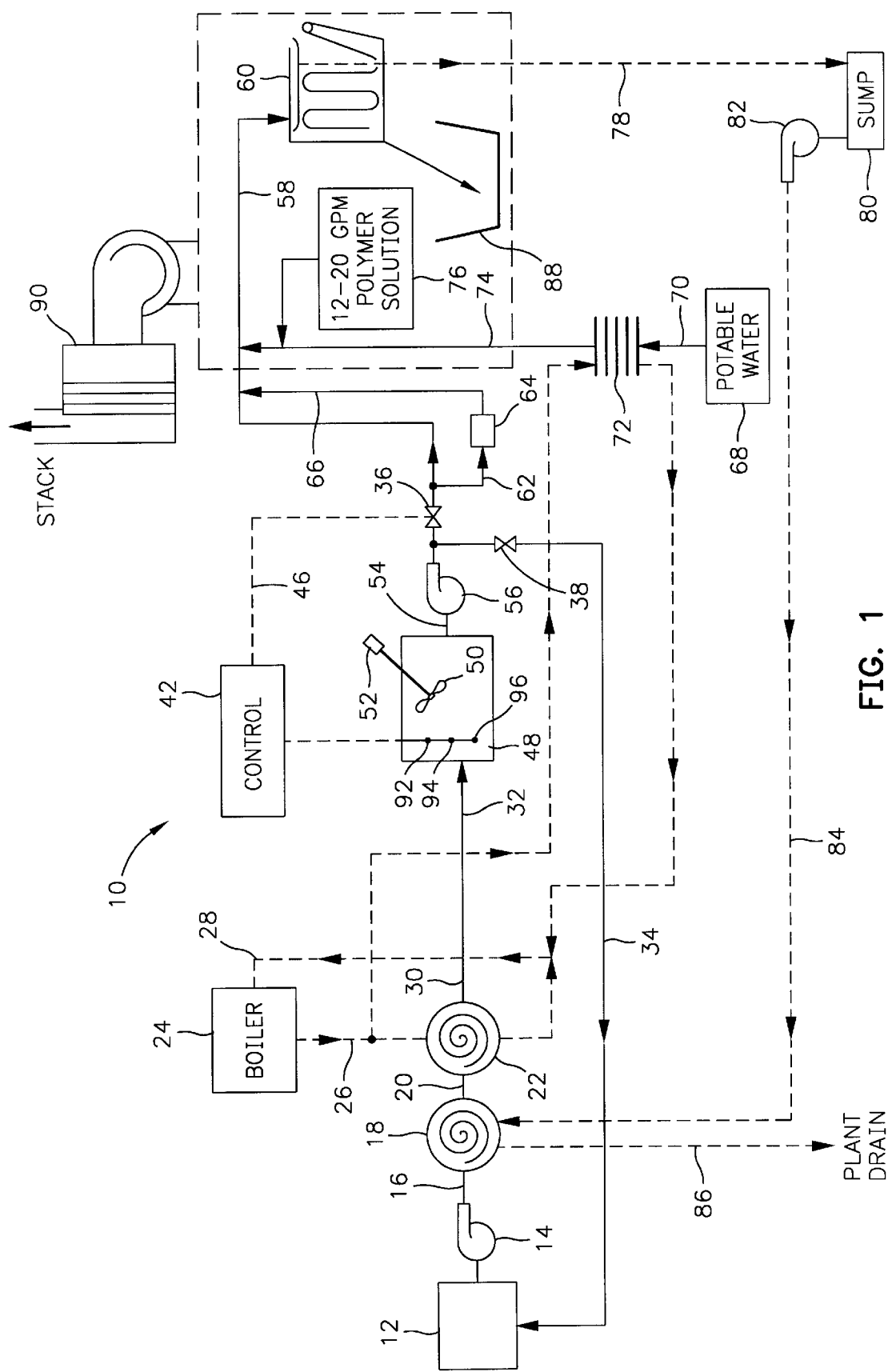
FIG. 1 is a view of a system in accordance with a preferred embodiment of the present invention.

The present invention was devised to provide a system to enable sewage to be economically treated and disposed of. The system provides a continuous flow pasteurization of sludge to eliminate pathogens so that the sludge may be used for fertilizer and/or soil amendment. Referring to FIG. 1 of the drawings, a system in accordance with the present invention is schematically illustrated and designated generally by the numeral 10. The system comprises a source of sludge such as an underground sludge holding tank 12 which receives sludge from an anaerobic/aerobic digester. The sludge is a slurry of solids in the range of about two to about seven percent (2–7%) in water as a carrier. A pump 14 delivers the sludge by way of a line 16 to a first heat exchanger 18 where it is heated to a first temperature. The sludge is them pumped by a conduit or line 20 to a second heat exchanger 22 where it is heated to the pasteurization temperature of about 140 to about 160 degrees Fahrenheit.

The first heat exchanger 18 is a preheater which receives its heat by way of extruded water from the plant dewatering process, as will be explained. The second heat exchanger 22 receives heat from hot water from a boiler 24 by way of lines or conduits 26. The heat supplied in the present system is by way of water at 180° F. for raising the temperature of sludge in the heat exchanger 22 to preferably about 160° F. Hot water from the heat exchanger 22 recirculates by way of line 28 back to the boiler 24 for reheating. The heat exchangers may be any suitable type that can transfer heat from water or steam to a sludge. Applicant has found spiral heat exchangers of the type available from Alfa-Lavel Thermal, Inc. to be particularly suitable.

The heated sludge which is a slurry of anywhere from about two to seven percent (2–7%) solids in water is maintained at preferably about 160° F. for a period of preferably about thirty minutes to kill all pathogens in the slurry. As illustrated, it flows by way of a line or conduit 30 to a detention tank or circuit 48 where it is maintained at about 160° F. for about thirty minutes. The slurry is then pumped by pump 56 from the detention circuit via conduit 58 which includes a junction with recirculating line 34, controlled by temperature responsive valves 36 and 38, which operate, if necessary, to recirculate the sludge slurry back through the heat exchanger. Recirculation may be necessary to ensure that it reaches and maintains the desired or predetermined pasteurization temperature of about 160° F. prior to sludge dewatering. When the sludge reaches the juncture of lines 58 and 34, sensors sense the temperature by way of conductors 46 at control system or panel 42 which monitors the temperature and operates valves 36 and 38 to recirculate the slurry, if necessary. If the temperature of the sludge is less than the predetermined minimum temperature, valve 36 closes and valve 38 opens to recirculate the sludge back to the intake to pump 14 where it is again passed through the heat exchanger 22 for further heating. The recirculating line can be either upstream or downstream of the detention tank or it can have both. However, in the preferred arrangement, it is downstream to ensure that all material passing through the detention tank has been maintained at the minimum required temperature for the required time.

When the sludge reaches a suitable temperature above its predetermined minimum pasteurization temperature in heat exchanger 22, it passes by way of conduit or line 32 into the detention circuit 48 which in the illustrated embodiment is a vertical tank having a mixing or stirring paddle or propeller 50 driven by a suitable motor 52. The slurry enters the detention tank 48 at the bottom thereof from line 32 and migrates in the tank toward the top or outlet for its thirty minute holding period until it reaches the top of the tank. The rotating propeller 50 assures suspension of the biosolids and acts against the flow of sludge toward the outlet and thereby prevents short circuiting. When the slurry reaches the top of the tank it passes out of the tank by way of conduit or pipe 54 to the inlet of pump 56 for further processing such as delivery to a dewatering system. The temperature of the slurry is checked at this point and recirculated back to heat exchanger 22 if necessary, to ensure its pasteurization temperature and period.

The detention tank system as illustrated has been proven by extensive testing to hold the slurry for the necessary minimum pasteurization time without short circuiting. In other words no unpasteurized slurry has been found to pass through the tank during these tests in normal operation. This has been validated through extensive fecal coliform, enteric virus, and helminth ova testing. Alternative detention systems or circuits such a baffled tank or an elongated circuitous pipe may be used to provide further insurance if desired. It will be appreciated that the sludge can be raised to a much higher temperature for a shorter time and achieve pasteurization. However, higher temperatures would require more energy resulting in higher costs and in most instances would not be economical.

The pump 56 delivers the pasteurized slurry by way of line 58 to a suitable dewatering system 60. It will be appreciated that any number of different suitable dewatering systems are available and may be utilized. The dewatering system of the present system is illustrated as a belt filter press. Alternatively, the pasteurized sludge or slurry is fed by way of a conduit 62 to a second anaerobic digester 64 where it is further digested and then passed by outlet line 66 to line 58 where it is then conveyed to the dewatering system 60.

A quantity of polymer is fed in solution such as in water from a source of water 68 by a conduit 70 to a heat exchanger 72 and a line 74. Polymer with a mix of 12–20 gal/min is fed from a source 76 into the conduit 58 for introduction and mixing with the sludge before it enters into the dewatering apparatus 60. This aids in the dewatering of the sludge.

The dewatering apparatus 60 is preferably a belt type filter press which presses the sludge between belts and rollers, collects and returns the extracted water by way of a conduit 78 to pump 80. This water is circulated by way of pump 82 in conduit 84 back to the preheater 18 to recover some heat from the water before it is discharged by way of conduit 86 for reclamation. This water is returned to the plant influent for processing to remove organic and nitrogen compounds.

The pasteurized sludge cake recovered from the dewatering apparatus 60 passes into a suitable storage bin or reservoir 88 for retrieval and disposal. The sludge forms a cake that is composed of 20–22% dry solids. The sludge cake is then, because of its pasteurization, completely devoid of pathogens and can now be distributed for agricultural purposes, such as fertilizer and/or soil conditioning. The sludge is maintained in the detention circuit 48 at a temperature of about 160° F. for a time of about 30 minutes to kill the bacteria and viruses therein. This system has been pilot tested and proven reliable and found to produce Class A biosolids, which is defined as free of pathogens. This system and process can be used to satisfy U.S. EPA Part 503 Regulations which define pasteurization of biosolids as that which are maintained at a 158° F. or higher, for at least 30 minutes.

The present pasteurization process has been tested and shown to produce Class A biosolids when heated to and maintained at about 160° F. temperature for a detention time of 30 minutes. Pilot testing results indicate Class A biosolids can be achieved at lower temperatures and detention times. Thus, pathogen-free Class A biosolids can be produced in the system of the present invention with very flexible operating parameters. This flexibility enables the parameters of operation to be adjusted for the most economical operation. The system provides a continuous flow processing system that can be built into sewage treatment plants for a continuous flow 24 hour per day continuous operation.

This system also provides a highly efficient economical operation for sewage treatment that produces Class A biosolids that can be disposed off without further processing, such as the traditional methods of composting. The system also removes much of the sulphur and other odor-causing components from the system at the dewatering operation with suitable scrubber system 90. Thus, it produces an environmentally compatible system. The system can be set up to operate automatically with the controller 42 having temperature monitoring means at strategic positions in the system, such as a plurality of sensors 92, 94 and 96, in the detention tank or circuit 48. The present system can be modified in a number of ways to produce the above described desired results.

The conversion of biosolids to class A increases their marketability and eliminates the management and site restrictions associated with class B materials. This process has also been found to enhance the dewatering process enabling the removal of a higher percentage of the water. This reduces the cost of transportation of the resulting biosolids product.

Figure 2:
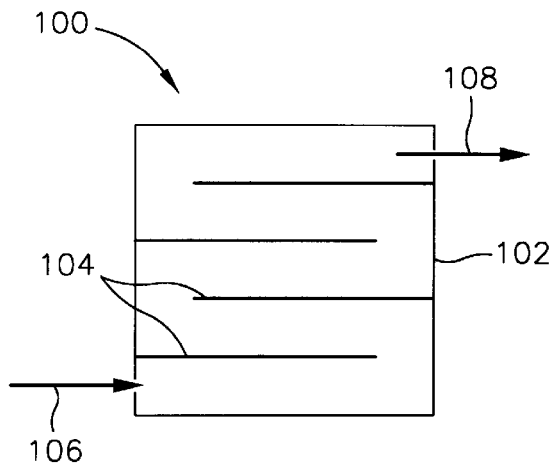
FIG. 2 is a diagrammatic illustration of an alternate arrangement of the pasteurization circuit.

Referring to FIG. 2, an alternate embodiment of the detention circuit is illustrated and designated generally by the numeral 100. This may take any number of suitable forms, but in the illustrated embodiment a reservoir 102 is provided with a plurality of baffles or walls 104 providing a circuitous or tortuous path from an inlet 106 to an outlet 108. This path would have a length sufficient that the slurry of sludge would maintain residence within the circuit for the predetermined necessary minimum time at the prescribed flow-rate. The slurry is forced to follow the entire path to the outlet, and ensures that no short-circuiting of the temperature residence time occurs.

Figure 3:
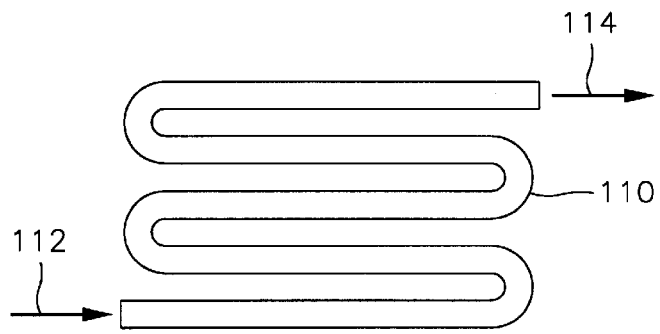
FIG. 3 is a diagrammatic illustration of a further embodiment of a pasteurization circuit.

Referring to FIG. 3, a further embodiment of the detention circuit is illustrated and comprises an elongated pipe or conduit 110 having an inlet 112 and an outlet 114. The conduit is formed in a circuitous path from the inlet 112 to the outlet 114. This path would have a length sufficient that the slurry of sludge would maintain residence within the circuit for the predetermined necessary minimum time at the prescribed flow-rate. The slurry is forced to follow the entire path to the outlet, and ensures that no short-circuiting of the temperature residence time occurs. These two embodiments may also be provided with suitable stirring means to insure that the solids remain in suspension.

Figure 4:
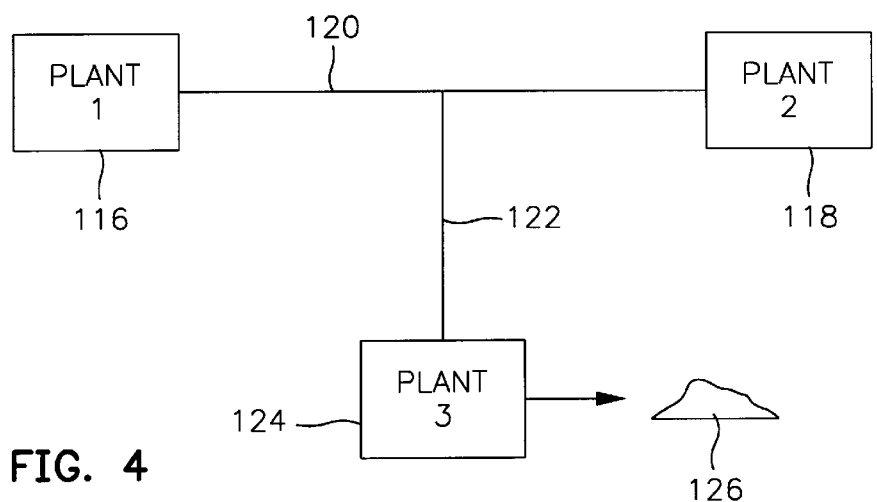
FIG. 4 is a schematic diagram illustrating a multi-plant processing system.

Referring to FIG. 4, a multiple plant system is illustrated wherein a plurality of plants 116 and 118 supply slurry from their digesters via pipelines 120 and 122 at a plant 124 having a continuous pasteurization system. The plant 124 processes the sludge to produce class A sludge that can be dewatered and accumulated in a pile 126 and subsequently economically disposed of. This system provides an arrangement for a metropolitan water district having a number of small wastewater treatment plants to invest in a single pasteurization system in accordance with the present invention. The pasteurization system can operate in a continuous flow process around the clock and provide improved economy for the entire district.

While I have illustrated and described my invention by means of specific embodiments, it is to be understood that numerous changes and modifications may be made therein without departing from the spirit and scope of the invention, as defined in the appended claims.

I claim:

1. A continuous flow sludge pasteurization system, comprising:
    a liquid flow system including a reservoir having an inlet and an outlet and means for establishing and maintaining a continuous flow of a liquid slurry into said inlet and from said outlet;
    a heat exchanger at said inlet for introducing heat into said slurry;
    a source of heat for introducing heat into said heat exchanger for heating said continuous flow of slurry to a predetermined minimum temperature;
    a rotating propeller positioned between said inlet and said outlet for acting against the continuous flow of slurry toward said outlet for maintaining said slurry in said liquid flow system at said predetermined temperature for a minimum period of about thirty minutes sufficient to kill all pathogens in said slurry; and
    dewatering means after said outlet for removing water from said slurry.

2. The system of claim 1 wherein said circulating circuit is a reservoir having an inlet at the bottom thereof and an outlet at the top thereof.

3. The system of claim 1 wherein said heat exchanger is a spiral heat exchanger.

4. The system of claim 1 wherein said heat exchanger includes a pre-heater.

5. The system of claim 1 wherein said dewatering means comprises a belt filter press.

6. The system of claim 1 wherein said dewatering means comprises a belt filter press.

7. The system of claim 6 further comprising means for recirculating said slurry to said heat exchanger for obtaining said minimum predetermined temperature prior to slurry dewatering.

8. The system of claim 1 further comprising means for recirculating said slurry to said heat exchanger for obtaining said minimum predetermined temperature prior to slurry dewatering.

9. The system of claim 8 further comprising a second stage anaerobic digester down stream of said circulating circuit.

10. The system of claim 1 further comprising a second stage anaerobic digester down stream of said circulating circuit.

11. A continuous flow sludge pasteurization system, comprising:
    a liquid flow system including a reservoir having an inlet and an outlet and means for establishing and maintaining a continuous flow of a liquid slurry into said inlet and from said outlet;
    a heat exchanger including a preheater at said inlet for introducing heat into said slurry;
    a source of hot water for supplying continuous heat to said heat exchanger
    for heating said slurry to a predetermined minimum temperature of about one hundred sixty degrees Fahrenheit;
    a rotating propeller positioned between said inlet and said outlet acting against the flow of said slurry toward said outlet for maintaining said slurry in circulation in said reservoir at said predetermined temperature for a minimum period of about thirty minutes sufficient to kill all pathogens in said slurry;
    dewatering means after said outlet removing water from said slurry; and
    means for circulating water obtained from said dewatering means through said pre-heater.

12. The system of claim 11 wherein said circulating circuit is a reservoir having an inlet at the bottom thereof and an outlet at the top thereof.

13. The system of claim 12 wherein said heat exchanger is a spiral heat exchanger.

14. The system of claim 13 wherein said dewatering means comprises a belt filter press.

15. The system of claim 14 further comprising a second stage anaerobic digester down stream of said circulating circuit.

16. A continuous flow sludge pasteurization process, comprising:

provinding a continuous flow circuit having an inlet and an outlet;

introducing a continuous flow of a liquid slurry into said circuit at said inlet;

introducing a quantity of heat into said slurry for heating said slurry to a predetermined minimum temperature of about one hundred sixty degrees Fahrenheit;

maintaining said continuous flow of slurry in said circuit at said predetermined temperature for a minimum period of about thirty minutes sufficient to kill all pathogens in said slurry while maintaining a continuous flow of said slurry from said outlet; and removing water from said slurry to produce a sludge.

17. The process of claim 16 wherein said step of providing a continuous flow circuit includes the steps of:

providing a reservoir having an inlet and an outlet; and providing a rotating propeller positioned at said outlet acting against the flow of said slurry toward said outlet.

18. The process of claim 17 wherein said step of introducing heat includes introducing said heat via a spiral heat exchanger.

19. The process of claim 17 wherein said step of dewatering is carried out by means of a belt filter press.

20. The process of claim 17 further comprising the step of circulating said slurry through an anaerobic digester prior to said dewatering step.

* * * * *